United States Patent [19]

Pitaru et al.

[11] Patent Number: 5,002,583
[45] Date of Patent: Mar. 26, 1991

[54] COLLAGEN IMPLANTS

[76] Inventors: Sandu Pitaru, 11 Einstein Street, Ramat Gan; Matitiau Noff, 5 Shkolnik Street, Rehovot, both of Israel

[21] Appl. No.: 894,849

[22] Filed: Aug. 8, 1986

[30] Foreign Application Priority Data

Aug. 13, 1985 [IL] Israel .................................. 76079

[51] Int. Cl.⁵ .............................................. A61F 2/28
[52] U.S. Cl. ........................................ 623/66; 623/16
[58] Field of Search ....................... 623/16, 18, 20, 21, 623/22, 23, 11, 10, 1

[56] References Cited

U.S. PATENT DOCUMENTS 4,202,055  5/1980  Reiner et al. .......................... 623/23
4,713,076  12/1987  Draenert ............................... 623/16

FOREIGN PATENT DOCUMENTS 0030583  6/1981  European Pat. Off. .......... 623/16 D
2502884  7/1976  Fed. Rep. of Germany ........ 623/23

Primary Examiner—David J. Isabella
Attorney, Agent, or Firm—Fleit, Jacobson, Cohn, Price, Holman & Stern

[57] ABSTRACT

The invention relates to implants, for use in human and in veterinary medicine. The novel implants form, after implantation, an integral structure with the surrounding tissues. The implants consist of a rigid core which is coated with a well adhering matrix, in which there are embedded collagen fibers, part of which protrude from the surface of said matrix. A wide variety of solid physiologically acceptable materials can be used. The matrix may optionally contain additives, such as fibronectin, platelet derived growth factor, bone morphogenic proteins, growth factors, vitamin D or hormones, or a combination of any of these.

12 Claims, 2 Drawing Sheets

STRUCTURE OF THE NOVEL IMPLANT

CORE

PLASTIC MATERIAL

COLLAGEN FIBERS

STRUCTURE OF THE NOVEL IMPLANT

CORE

PLASTIC MATERIAL

COLLAGEN FIBERS

COLLAGEN IMPLANTS

BACKGROUND OF THE INVENTION

Modern medicine utilizes artificial implants in order to surgically replace whole and/or parts of organs and tissues that have been affected by either disease or trauma and consequently, have become non-functional. For example, auditory ossicles of the middle ear, eye lenses, teeth, and joints can be replaced by artificial implants. All artificial implants adopted are made of biocompatible materials—that is, materials that have been proven: (a) to be non-toxic for either the surrounding tissues or other organs of the host; and (b) not to raise any immunological response that could cause rejection of the implant. However, to the best of our knowledge, all of these materials do not have any biological properties and therefore, are not identified by the host as an integral part of the body. The implication of this fact is that the implant will not be affixed to the surrounding tissues by a biological bond such as is the case when either a bone or a skin graft is performed. Consequently, the anchorage of known artificial implants to the surrounding tissues is achieved by physical and mechanical means (screws, cements and porous surfaces). Biological materials (collagens and others) have been used to coat the surface of these implants in order to enhance tissue repair, growth and adaptation at the implant-tissue interface. These are absorbed or degraded by the surrounding tissues. That leaves the mechanical anchorage as the only method known to date which enables the securing of artificial implants to the surrounding tissues for a limited period of time. The evidence accumulated indicates that the shearing forces which acts at the implant-tissue interface, during the function of the implant, causes the loosening of the mechanically anchored implants. It is thus believed that the lack of a *biological bond* between the surface of the implant and surrounding tissues is the main reason for this failure.

SUMMARY OF THE INVENTION

There are provided novel prosthetic devices, for surgical implantation into human or animal bodies. The novel implants comprise a rigid, advantageously solid core provided with a surface layer covering at least part of its surface, which surface layer comprises a matrix wherein there are embedded collagen fibers, the ends of at least part of which protrude from the surface of this layer. The surface layer comprises advantageously a polymeric matrix in which collagen fibers are embedded, and forms a biological substrate which results in unique properties of the implants. The core material can be any suitable rigid material: plastic, metal, metal alloy, ceramic, reinforced material or the like, which has the required biocompatibility. Consequently, a long lasting biological bond is formed between the surgically implanted device and the host tissues. The biological substrate is secured by either chemical or mechanical means to the solid material which forms the core of the prosthetic device of the invention.

DETAILED DESCRIPTION OF THE INVENTION

The surgical prosthetic device of this invention comprises two components forming an integral structure: (i) a main body or core, and (ii) a biological substrate.

(i) The main body or core of the prosthetic device

The main body or core is of a predetermined size, shape and material, depending upon the prosthetic device properties desired, as subsequently described below.

(ii) The biological substrate of the prosthetic device

The biological substrate forms a long lasting biological bond or anchorage between the surface of the surgically implanted prosthetic device and the host tissues. The biological substrate, which comprises advantageously a polymeric matrix in which collagen fibers are embedded, is secured to the main body or core to form a number of layers anchored together, thus forming an integral structure. Although the biological substrate forms an integer, for the purpose of describing the present invention, a structure having three layers is set out by way of example in the following:

(a) An inner layer of about 0.5 to about 3 mm thickness, preferably a plastic polymer. During fabrication of the biological substrate, the plastic polymer is bonded, either mechanically or chemically, to the core of the prosthetic device.

(b) An intermediate layer 0.2 mm to about 5 mm thick composed of the same plastic polymer as in (a) and of collagen fibrils, 0.1–1 u in diameter which are arranged either in a three-dimensional mesh or in bundles 0.01 to 1 mm thick. The spaces between the collagen fibrils forming such mesh or bundles being occupied by the plastic polymer. Moreover, during the processing of the biological substrate, the plastic polymer infiltrates each of the mesh fibrils. That means that the micro-fibrils and possibly the molecules of the collagen fibrils and fibers are impregnated with the plastic polymer. This collagen polymer interaction is achieved by the unique process of production of the biological substrate as described below.

(c) An outer layer 0.5 to 2.5 mm thick consisting of either a mesh of collagen fibers or bundles of collagen, the fibrils of which are a continuity of the fibrils in the intermediate layer. Thus, the same collagen structure is embedded within the polymer matrix of the intermediate layer of the biological substrate and it constitutes the outer layer of the substrate.

The special relation between the plastic polymer and the collagen fibers in the intermediate layer described in (b), provides an extremely strong anchorage for the collagen fibers of the outer layer. Experiments performed in order to test the bond strength between the collagen mesh and the plastic polymer indicate that the collagen fibers rupture before they can be separated from the plastic polymer when push-out mechanical force is applied.

The outer layer of the biological substrate is adapted to serve as the means by which the substrate is biologically anchored to the surrounding host tissues. This is made possible due to the fact that the collagen structure of the outer layer forms a biological matrix that stimulates the host tissues which it makes contact with, to ingrow between and to bind to its collagen fibers. The practical meaning of the biological bond is that the collagen fibers of the collagen mesh become an intergral part of the host tissues with which they interact.

Since the same collagen fibers are also strongly secured to the polymer matrix, the biological substrate of this invention becomes biologically affixed to the host tissues. It is evident from the above that the biological substrate is used as an unique means to biologically anchor the novel prosthetic device to host tissues.

In the long term, it is expected that the collagen fibers of the outer layer of the biological substrate that form an integral structure with the host tissues will be replaced by collagen fibers produced by the host tissue cells. However, experimental work indicates that the continuity between the newly formed collagen fibers of the outer layer and the collagen fibers in the intermediate layer will be preserved. Thus, the biological anchorage of the prosthetic device of this invention to the host tissue will be also preserved during the process of collagen replacement. Moreover, this preservation is made possible despite the fact that the "anchorage ropes," that is, the collagen fibers of the outer layer are continuously renewed consequent to the physiological turnover of the host tissues.

The biological anchorage of the prosthetic device of this invention to the host tissue is superior to the mechanical anchorage of the prior art. Further, the biological anchorage overcomes the weakness problems associated with prior mechanically bonded artificial implants. The two reasons for this are: First, the host tissues identify the outer layer of the biological substrate as a biological material. Consequently, this material—namely, the collagen fibers, are incorporated within the host tissue and becomes an integral part with same. Since these collagen fibers are continuously renewed during the physiological turnover of the host tissue and are also embedded within the plastic polymer of the biological substrate as described above, a long lasting biological bond is formed between the artificial implant and the host tissue. Second, the shear forces that develop at the implant-tissue interface are attenuated and translocated within the host tissue by the collagen fibers of the biological substrate of the prosthetic device of this invention. Therefore, the main factors that cause the loosening of the mechanically secured artificial implants are eliminated as a result of the novel biological properties of the prosthetic device of this invention and a long lasting function of the implant is made possible.

Materials which can be used for the production of surgical prosthetic devices of the invention are:

a. For the production of the main body of the prosthetic device (its core):

1. Metal and Metal Alloys:

Metallic materials are used when the implant must withstand stress, shearing and torsion forces of considerable magnitude. Examples of such metallic materials are: austenitic stainless steel, titanium, titanium alloys and cobalt alloys. Metallic materials are used for the fabrication of orthopedic and dental implants.

2. Plastic Substances:

Plastic materials are used to answer special biophysical demands. For example: (a) the main body of a surgical ophtalmic implant is made of a plastic material like polymethymethacrylate that enables light to pass through; (b) high density polyethylene is used for the fabrication of articular surfaces of joint implants in order to answer low friction demands. Examples of suitable plastic materials are: acrylics such as like polymethylmethacrylate,—aromatic acrylics, cyanoacrylate; silicone rubbers; polyethylene derivatives; polyacetal derivatives.

3. Ceramic Materials

Ceramic materials are used for the fabrication of articular surfaces of surgical joint implants when low friction and low wear surfaces are requested.

4. Fiber Reinforced Plastic Polymers

Fiber reinforced plastic polymers are an alternative to the metallic materials for the fabrication of the main body of the surgical prosthetic device. Examples of these are: carbon reinforced polymers, carbon reinforced carbon, glass fibers reinforced polymer, plastic fibers reinforced polymer, collagen fibers reinforced polymer.

b. Materials used for the fabrication of the biological substrate of the prosthetic device 1. Plastic Polymers Examples for the plastic polymers used for the fabrication of the biological substrate are: acrylate derivatives, silicone rubber derivatives, polyethylene derivatives, polyacetal derivatives. When required, such plastic polymers can be reinforced by fibers like: carbon fibers, glass fibers, plastic fibers, collagen fibers.

2. Collagens

Examples for collagens used for the preparation of the biological substrate are collagen type I, collagen type II, collagen type III.

3. Substances used to enrich the collagen fibers

Fibronectin, platelet deriving growth factor, bone morphogenetic proteins, Vitamin D and its metabolites, growth factors, hormones, collagens types IV, V, VI, VII, VIII, IX, X.

Required properties of the materials used for the fabrication of surgical prosthetic devices of this invention Required properties of the materials used for the fabrication of the main body Biological properties—The material of the main body should be a biocompatible material without cytologic or toxic effects on any of the body tissues.

Mechanical properties—The main body should have adequate mechanical strength to withstand forces that develop consequent to the long lasting implant function either within the main body or at the interfaces between the main body and other movable or non-movable parts of the prosthetic device.

Physico-chemical properties—(a) The main body should be insoluble in any of the body fluids, thus preventing its degration when implanted into the host. (b) The main body should not absorb body fluids nor change its dimension when implanted within the host.

Required properties of the materials used for the fabrication of the biological substrate The plastic polymer:

Biological properties—The plastic polymer should be a bicompatible material without cytologic or toxic effects on any of the body tissues.

Mechanical properties—The plastic polymer should have adequate mechanical strength to withstand forces that develop consequent to the long lasting implant function either within the polymer itself or at the interfaces of the biological substrate with the main body of the implant. (This property is required to ensure the safe securing of the biological substrate to the main body of the prosthetic device when the linkage between the components is mechanical.)

Physico-chemical properties—(a) In its solid state, the plastic polymer should be insoluble or non-resurbable in any of the body fluids, preventing its degradation when implanted into the host. (b) The plastic polymer should not absorb body fluids nor change its dimension when implanted within the host. (c) In order to allow for the embedding of the collagen fibers within the plastic polymer, it should be possible to convert the latter from a liquid monomer to a solid polymer. The conversion should be preferably performed at a temperature not exceeding 38° C., thereby preventing the denaturation of the collagen fibers. (d) The plastic material in its liquid state, and during its conversion to the solid state, should have the property of chemically binding to a solid surface of either the same material or similar plastic materials. (This property is required to enable the chemical linkage of the biological substrate to the main body of a prosthetic device made either of similar or of the same plastic materials as that of the biological substrate.)

The Collagen:

Mechanical properties—The collagen fibers of the collagen mesh and/or bundles should be strong enough to withstand the forces that develop during the function of the implant. The mechanical strength of the collagen depends on three factors: (a) the width of the individual collagen fibers; (b) the cross-linking between the collagen molecules within a fibril and the cross-linking between the microfibrils and fibrils; and (c) the density of the mesh and/or bundles (the number of collagen fibers per unit volume). The mechanical strength of the collagen of different implants varies according to the variation in stress and shear forces that exist at the tissue implant interface. For example, the required magnitude of the mechanical strength of a collagen component that is part of a surgical prosthetic lens should be smaller than that of a surgical prosthetic tooth.

It is possible to control and regulate the mechanical strength of the collagen component of the biological substrate, when this is prepared in vitro from a molecular solution by regulating the process of fibrilation and the degree of intermolecular and interfibrillar crosslinking.

Biological properties—The collagen fibers should preserve their well known biological properties following the partial embedding of the collagen and/or bundles within the polymer matrix of the intermediate layer of the biological substrate.

Biologic substances for the enrichment of the collagen mesh of the third layer of the biological substrate:

Collagen is known to bind different biologic substances. These substances are used to modulate the events at the implant host tissue interface during the development of the biological bond.

The biological substances should be non-toxic for any of the body organs or tissues.

The preparation of the biological substrate and its binding to the main body of the prosthetic device:—General Considerations The preparation of the biological substrate of this invention is performed simultaneously with its binding to the main body. In this respect, the main body may consist of two types of material: (a) material that can form chemical bonds with the plastic polymer of the biological substrate. Examples of such materials are different biocompatible plastic polymers that have the required physico-chemical properties for being used for the fabrication of a specific implant; and (b) material that cannot form chemical bonds with the plastic polymer. The surface of artificial implants made up of this type of material should be designed to enable the mechanical binding of the plastic polymer of the biologic substrate. Examples of such materials are different metal alloys.

The first step of preparation of the biological substrate is to bind a layer of the plastic polymer to the surface of the solid core. This layer constitutes the inner layer of the biological substrate described above. To accomplish this, the plastic component of the biological substrate is applied in either its liquid state or as a paste to that surface of the implant that is designated for the anchorage of the implant to the host tissues. There, the plastic polymer of the biological substrate is converted to its solid state. The hardening process may be initiated either by a chemical or physical catalyst such as peroxide, ultraviolet light or heat. During the hardening process, the plastic material of the biological substrate becomes bound to the material of the main body consequent to the formation of either mechanical or chemical bonds.

The second step is the preparation of the collagen structure. A collagen mesh is prepared from a molecular solution of collagen. The type (collagens type I, type II or type III or any combination of these) and source of collagen can be varied according to the type of the recipient host tissue and the desired characteristics of the biological bond. By varying the pH and the temperature of the solution, its ionic composition and concentration, it is possible to control the size of the collagen fibers. A structure of type I collagen bundles is obtained from a tendon. Individual bundles are obtained by enzymatic (trysin and hyaluronidase) followed by mechanical separation. The individual collagen bundles are trimmed to a length of 1–5 mm, subjected to enzymatic treatment (trysin, hyaluronidase) in order to remove glycoproteins and proteoglycans, washed and dialyzed against distilled water.

The collagen mesh is stabilized by changing the aqueous solution in which it was prepared with 70% ethyl alcohol. The mesh of collagen fibers is thus gradually dehydrated, and can be preserved in a solution of an organic solvent such as ethyl alcohol, either, chloroform or a mixture of such solvents.

The third step is the partial embedding of the collagen aggregate within the polymer matrix of the biological substrate; that is, the preparation of the intermediate and the outer layers of the biological substrate. In order to do this, the collagen mesh or the collagen bundles are immersed in a solution of monomer of the plastic material of the biological substrate. This is done in order to imbue the collagen fibers with a monomer, thus replacing the organic solvents in the mesh. Then a layer of paste of the plastic material is applied to the previously prepared layer of solid plastic polymer. The thickness of this second layer may vary according to the width of collagen structure that has to be embedded within the plastic polymer, this depending upon the biomechanical properties required to be obtained. While the plastic material is still in the liquid state, the collagen mesh and/or bundles are removed from the monomer solution and partly embedded within the paste of the plastic material. Then the plastic material is cured. During the process of hardening, the outer part of the collagen mesh and/or bundles is washed continuously with an organic solvent to remove the excess plastic monomer.

The temperature of the plastic material should not exceed 38° C. during the hardening process in order to prevent the denaturation of the collagen fibers.

Prior to and following the embedding procedure, the fibers of the collagen-containing structure may be subjected to a process of intermolecular and/or interfibrillar cross-linking. This can be achieved by exposing the collagen fibers to either vapors of gluteraldhyde, to ultraviolet irradiation or to gamma wave irradiation.

A mold is prepared which is according to the shape of the collagen mesh before this is partially embedded in the polymer matrix.

A solution of Collagen I, prepared as set out above is cast into the mold, and after fibrillation and formation of the collagen mesh the collagen structure is fixed, dialyzed exhaustively, dehydrated and dried at the "critical point", i.e. under conditions of temperature and pressure where the collagen undergoes no appreciable shape change. A polymer paste is prepared and applied to those parts of the collagen mesh which are to be embedded therein. By varying the viscosity of the polymeric composition it is possible to vary the depth of penetration into the mesh. At this stage the polymer is cured so that part of the collagen fiber protrudes from the surface.

Collagen is the basic biologically active material of the biocompatible substrate of this invention. One prominent quality of the biological substrate is its ability to serve for the attachment and growth of cells. This property of the biological substrate was tested in an in vitro system. It was found that the ability of the collagen mesh of the biological substrate to serve as a substrate for cell attachment and growth has been preserved during the preparation of the substrate and that it is identical to that of demineralized collagen of either bone or teeth.

Examples of use of the novel surgical prosthetic device of this invention:

(a) Prosthetic devices of the invention may be used as artificial implants designed and designated to replace non-functioning auditory ossicles of the middle ear. The main function of such implant is to transmit the vibrations elicited by the tympanic membrane to the perilymphatic fluid of the inner ear. To perform this function, the implant must be affixed at its opposing extremities to the inner side of the tympanic membrane and either to the base of the stapes bone or to the oval window of the bony vestibule. The implant consists of a main body and the biological substrate of this invention, which may either cover the entire surface of the implant or may be located at the opposing extremities of the implant where the biological substrate serves as its biological anchorage to both the inner side of the tympanic membrane and the base of the stapes bone. In the event that the implant cannot be affixed to the base of the stapes, but instead is attached to the oval window, then the biological substrate is located only on that part of the implant that must be anchored to the tympanic membrane. In the event that all of the implant surfaces are covered by the biological substrate, the implant is covered by a thin layer of connective tissue and epithelium that binds to the collagen mesh of the biological substrate. These tissues are continuous at the extremities of the implant with the tissues of the recipient sites. Thus, the implant becomes an integral part of the host tissues. This type of biological anchorage enables the lifelong function of the described implant which has superior properties as compared with prior used artificial implants that were mechanically anchored.

(b) An additional use is in the ophthalmologic field. Two types of artificial implants were introduced in this field: artificial lenses and artificial corneae. Both are mechanically secured to the recipient site. Failure of these implants, particularly the cornea, are consequent to their detachment from the recipient tissue. To date, surgical artificial lenses are the main implant in this field and implantion of artificial cornea has been abandoned.

Generally, the artificial cornea and lens of this invention are either biconvex or concave and convex discs. The disc, which is the main body, is made of a material that has the required optical properties, like polymethylmethacrylate and, or glass. The peripheral rim of the disc is indented and comprises the biological substrate, which is chemically bound to the equatorial periphery of the disc by the process described above. The peripheral indentation serves as the mechanical retention of the implant until the biological bond between the artificial cornea or the artificial lens and the connective tissue of the sclera or the posterior capsule of the lens, repectively is formed. The biological anchorage, once formed safely secures such implants to the surrounding supporting tissues.

(c) Prosthetic devices of this invention can be used in the field of dental implantology. Three types of implants are presented:

(1) Artificial implants designated to provide additional support to teeth that become mobile as a result of periodontal disease. Such implants are conically-shaped and are implanted into the periapical bone through the root canal of the tooth. In order to receive the implant, both the root canal and the periapical bone are mechanically trimmed with the use of an adequate set of reamers and files. The main body of the implant is made of a metallic material like cobalt alloy, Vitallium (Trade Mark), titanium or titanium alloys. The implant is secured to the tooth by the cementation of that part of the implant main body located within the root canal of the tooth. That part of the implant main body which extends beyond the apex of the tooth into the periapical bone comprises on its outer surface a biological substrate. The collagen fibers of the outer layer of the biological substrate are enriched by biological substances known to enhance the migration, attachment and proliferation of fibroblasts. These cells migrate from the apical periodontal ligament and from the adjacent bone to colonize the collagen mesh of the outer layer of the biological substrate to form a ligament-like structure between the surface of the implant and the surrounding periapical bone. Since the collagen fibers of the collagen mesh become an integral part of the fibrous component of this ligamentous structure and since this component is also embedded within the periapical bone, a fibrous anchorage of the implant to the periapical bony socket is obtained. This anchorage has similar properties to that provided by the periodontal ligament which is the tissue that normally anchors and supports the tooth in its socket. The additional support gained by the use of the implant of the invention assists in stabilizing the mobile tooth and prevents its loss.

(2) A second type of novel artificial dental implant of this invention is designated to replace: (a) teeth that are extracted as a result of loss of tooth material due to caries or to endodontic failure; and (b) teeth that are avulged as a result of trauma. A prerequisite for the use of this type of dental implant is the existence of sufficient supporting alveolar bone to which remanents of vital periodontal ligament was left following either the extraction or avulsion of the tooth. This type of implant has the shape of a root of a single rooted tooth or roots of multirooted teeth. The implant main body is made of a metal that has the required properties mentioned above. The peripheral part of the main body supports the biological substrate. Following either the extraction or avulsion of a tooth, an adequate implant of this type is implanted within the alveolar socket. A ligamentous structure similar to that described in (c) (1) biologically anchors the implant to the bony socket and to the gingival connective tissue. The occlusal part of the implant is designed to accommodate a post that bears a supragingival crown-shaped structure prepared for receiving a prosthodontic restoration. This structure is used to secure the implant to adjacent teeth until the biological anchorage is formed.

Similar dental implants have been used in prior art suggestions. However, these implants are made only of a metallic material. Thus, the nature of the anchorage of the implant to the periapical bone was mechanical, relying on the adaptation and adherence of the bone tissue to the surface of the implant. As discussed above, the failure of these prior suggested implants is due to the shearing forces exerted at the implant bone interface by the micromovements performed by these implants during the function of the tooth. These forces cause the resorption of bone adjacent to the implant surface, its replacement by connective tissue and consequently the loss of anchorage. The ligamentous anchorage obtained by the use of implants of the invention allows micromovements at the implant-ligamentous tissue interface. Moreover, these micromovements are considered to be a prerequisite for the maintenance of homeostasis of the ligament and of the bone into which the implants are anchored.

(3) The third type of novel surgical dental implant of this invention is designated for implantation in edentulous areas. This implant has an adequate design for implantation in areas where the amount of bone available for supporting the implant is limited. The implant consists of an infragingival part and a supragingival part. The infragingival part comprises the biological substrate of the invention and is designated to provide the biological anchorage of the implant to the bone and gingiva. The properties of the collagen of the biological substrate stimulate the rapid growth of bone towards the implant surface. Consequently, the free collagen fibers of the substrate are embedded within newly formed tissue, thus securing the implant to the surrounding bone and gingiva. The supragingival part is designed to receive a non-surgical prosthesis. The main body of the implant consists of a metallic material as described above.

(d) Novel surgery prosthetic devices of the invention can be used in the field of plastic and reconstructive surgery. Three types of implants are presented by way of example:
(1) Artificial implants designated to replace relatively thin hard matrix of tissue such as cartilage of the ear and cartilage and bone of the nose.
(2) Artificial implants designated to be added to the body tissue thus creating new appearance of the organ or the body.
(3) Artificial implants designated to replace inner body hard structures such as parts of cartilage of trachea and/or bronchi of the respiratory tract system.

The implant must be affixed with its entire outer surface to the surrounding tissue. The main body of the implant can be made of a plastic polymer such as polymethylmetacrylate and is completely covered by the biological substrate. As a result of the development of the biological anchorage, the implant is incorporated within the host tissues.

The biological anchorage of the implant to the surrounding tissues prevents the encapsulation and cyst formation around the implant as is the case when implants of prior arts are used.

The design of the implant is made according to functional, aesthetical and anatomical demands. The implant can be designed to replace a missing nose or can have a tubular or part of a tubular wall configuration in order to replace part of the trachea, thus keeping the airways open. It can also be designed to replace part of the sclera following its surgical resection or traumatic perforation.

(e) Novel surgical prosthetic devices of this invention are used in the field of orthopedic surgery. Three types of implants are presented as example:
(1) Implants designated to replace parts of bone. The main body can be made either from metallic materials or from plastic or plastic composite. The main body is covered completely by the biological substrate allowing the surrounding tissues to bind biologically to all of its outer surface. The incorporation of the implant into bone tissue is full and complete.
(2) Implants designated for the total or partial replacement of joints. Generally, the implants main body is constructed in accordance to the up-to-date state of prior art. The artificial implant consists of two parts with articulation between them to form a joint. Each part exhibits an extrabony and an intrabony aspect. The extrabony aspect bears the articular surface. The part of the main body incorporated into the bone is covered by the biological substrate which enhances the bone surrounding the implant to grow and fill the defects produced during the preparations of the recipient site. The free collagen fibers of the biological substrate are embedded within the newly formed tissue, thus securing the implant to the surrounding bone.
(3) Implants designated to enable the activation of a non-surgical limb prosthesis attached to the remanent of an amputated limb. The implant is implanted into a muscle of a remanent amputated limb. The implant consists of either a plastic or metal material covered completely by the biological substrate. The biological substrate enables the securing of the implant to the muscle connective tissue. Either a plastic or metal rope emerging from the implant transfers the contraction forces to the non-surgical limb prosthesis enabling its activation. The biological anchorage of the device to the muscle tissue withstands the tensional forces applied on the implant during the activation of the non-surgical limb prosthesis. This novel type of implant allows for a simple and physiological activation of a non-surgical limb prosthesis that can mimic physiological limb movements.

(f) Novel surgical prosthetic devices of this invention may be employed to connect internal tubular systems of the body to external treatment devices. The implant consists of either a metal or a plastic ring that is partly embedded within the body and partly projects above the skin. The biological substrate is bonded to the peripheral surface of the embedded part of the ring and to its internal rim. The biological substrate ensures the biological securing of the tissue of the tubular systems and those of the skin and of other tissues of the body wall to the ring surface. The biological securing of the device is required in order to obtain a complete sealing at the host tissue-implant interface and thus preventing (a) leakage of body fluids and or materials from the tubular systems into the surrounding tissues; (b) loosening of the implant; and (c) the development of inflammation and infection at the site of implantation.

EXAMPLE I

This example illustrates the formation of a surgical prosthetic device designated to withstand load.

A femoral metal stem of a knee joint prosthesis made of VITALLIUM that exhibits a rough surface (similar to PCA prosthesis) is degreased, cleaned and dried. A commercial radiolucent polymethylmethacrylate (PMMA) (Simplex P. by Northill Plastics Inc., England) is used. 20 cc of liquid monomer of this material is mixed with 40 gr of powdered partial polymerized PMMA and the obtained loose paste is centrifuged for 3 min at 3000 rpm. The centrifuged mixture is held in a mould around the rough surface of the femural stem and let to harden for 10 days. All of these steps are carried out at 4° C. Thus a 3 mm thick uniform layer of PMMA bonded to the metal stem is obtained.

A gelatinous mesh of type I human collagen in a 20 ml aqueous solution is prepared according to the method described by Williams et al. (1978, 1979). The concentration of collagen is approximately 3.5-4 mg/ml.

The gel is transferred into a dish so that a 5 mm thick layer is obtained. This layer is irradiated with a 100 W ultraviolet lamp for 60 min and then dehydrated in a series of ethanols (50, 70, 80, 90, 95, 100% solution for half an hour in each solution). The absolute ethanol is replaced by liquid monomer of methyl methacrylate that contains 90 ppm of hydroquinone. The layer of collagen gel is removed from the liquid monomer and placed onto a flat surface. A 2-3 mm thick layer of PMMA paste, prepared as described above, is applied on the surface of the collagen layer and let to stay for 10 min at 4° C. Then, the side comprising the paste of the composite preparation of PMMA and the partly embedded collagen is applied to the surface of the PMMA coated metal stem. The product is immediately immersed into a shacking bath of absolute ethanol at 21° C., for 1 hour. Using this procedure one can obtain a biological substrate having a thickness of 7-8 mm. The free collagen layer is 2-3 mm thick, the PMMA layer comprising the embedded collagen is 2-3 mm thick and the layer of PMMA attached to the femural stem is 3 mm thick. Following the hardening of the PMMA paste, the product is preserved in absolute ethanol until used.

EXAMPLE II

The preparation of an Artificial Lens

This example illustrates the preparation of a prosthetic device that consists of a plastic core to which the biological substrate is attached. A commercial artificial lens made of acrylic can be used. The peripheral rim of the lens is conditioned with liquid methyl methacrylate monomer for 5 min. A 0.5 mm layer of loose paste of PMMA prepared as in Example I is applied to the peripheral rim of the lens. A 1 mm thick layer of collagen mesh is prepared, dehydrated, and maintained in absolute ethanol as described in Example I. A strip of collagen mesh having the same width as that of the peripheral rim of the lens is cut out from the 1 mm thick layer of collagen and is applied to the 0.5 mm thick layer of PMMA paste immediately after this has been applied to the peripheral rim of the lens. Following completion of the polymerization, the solid PMMA is bonded chemically to the acrylic lens and its superficial part (0.5 mm in thickness) comprises part of the collagen mesh of the biological substrate. A 0.5 mm thick layer of free collagen mesh attached to the peripheral rim of the lens is obtained using this procedure.

EXAMPLE III

The Preparation of a Dental Implant

This example illustrates an implant that penetrates through the body wall—gingiva, and connects an internal part of the body—the bone of the jaw, to an outer device—a dental prosthetic device.

A metallic core made of titanium is used to prepare the implant. The core is prepared as one integer using a routine casting procedure. The core consists of three parts:

(a) An internal part consisting of:
  (1) an horizontal suprabony plate, the dimensions of which are 10-20 mm by 3-5 mm by 0.5-1 mm
  (2) a wedge-shaped infrabony part, the bases of which is continuous with the lower aspect of the suprabony plate. The dimensions of the wedge are: the length and width of the wedge at its base are 1-2 mm less than those of the suprabony plate to which it is attached; the height of the wedge is 5-10 mm. The angle of convergence of the lateral aspects of the wedge is 75° relative to the plane of the suprabony plate. The tip of the wedge exhibits a round shape. The surface of the internal part of the core is indented.

(b) An intermediate part which is cylindrical having a diameter of 3-5 mm and a height of 3-4 mm. The cylinder is located in the center of the superficial aspect of the horizontal plate of the internal part. The peripheral aspect of the cylinder exhibits two types of surfaces: the deeper part (2-3 mm) is indented, and the superficial part (1-2 mm) is highly polished.

(c) A supragingival or intra-oral part is directly continuous with the intermediate part. It has a truncated conical appearance. The larger base of the truncated cone has the same diameter as that of the cylinder of the intermediate part and the diameter of the smaller base is 0.5-1 mm less.

A 0.5 mm thick layer of either PMMA paste or of a commercial composite of Bis-gamma methyl acrylate and glass fibers are attached to the indented surface of the titanium core using the method described in

EXAMPLE I.

A 1 mm thick layer of collagen mesh in liquid monomer of one of the above mentioned plastics is coated with a 1 mm thick layer of paste of the same material previously attached to the titanium core and is attached to the core as described in Example I.

Using this procedure, a 2.5 mm thick biological substrate attached to the titanium core is obtained. The collagen free layer of the substrate is about 0.5 mm thick, the layer of plastic material comprising the collagen is 1 mm thick and the deepest layer of pure plastic material is 1 mm thick.

It should be mentioned that the peripheral surface of the intermediate part of the implant serves two purposes:
(1) The deepest part bearing the biological substrate is designated to serve for the biological attachment of the connective tissue of the gingiva to the implant surface.
(2) The superficial part that exhibits a highly polished surface is designated for the attachment of the epithelial component of the gingiva to the implant surface.

The development of a long standing attachment of both the epithelial and mesenchymal components of the gingiva to the implant surface is a prerequisite for the development of a perfect seal at the site where the implant penetrates through the body wall to communicate to the external environment. This seal is required in order to prevent infection and inflammation at the implant-lost tissue interface and thus to ensure the long standing function of this type of implant.

I claim:

1. An implant for surgical implantation in human or veterinary medicine, adapted to form after implantation an integral structure with surrounding tissue, comprising in combination a rigid core of predetermined size and shape, at least part of the surface of which is coated with a non-resorbable polymeric matrix in which there are embedded and anchored collagen fibers, with at least part of the fibers protruding from the surface of said polymeric matrix for forming after implantation a firm bond with said surrounding tissue.

2. The implant according to claim 1, wherein the material of the core is selected from the group consisting of a metal, a metal alloy, a ceramic, a polymer and a reinforced material.

3. The implant according to claim 1, wherein the polymeric matrix supporting the collagen fibers has a thickness of 0.5 to 10 mm.

4. The implant according to claim 1 wherein the collagen fibers in the matrix form a three-dimensional network, and wherein the collagen fibers constitute from 10 to 70 weight percent of the polymeric matrix.

5. The implant according to claim 1, wherein the matrix applied to the rigid core comprises a three-layered structure which, starting with the rigid core, includes a non-resorbable polymer first layer bonded to the rigid core, a second layer formed by said non-resorbable polymeric matrix wherein there are embedded and anchored said collagen fibers forming a collagen network, the interstices of the collagen network being filled with said non-resorbable polymer, and an outer third layer formed by the part of said anchored collagen fibers protruding from the polymeric matrix.

6. The implant according to claim 1, containing adjuvants and auxiliaries enhancing the properties of the collagen, selected from fibronectin, platelet derived growth factor bone morphogenic proteins, Vitamin D or a metabolite thereof, growth factors and hormones.

7. A process for the production of an implant for surgical implantation in human or veterinary medicine, adapted to form after implantation an integral structure with surrounding tissue, which comprises the steps of providing a rigid body of predetermined size and shape, bonding to at least a portion of a surface of the body a non-resorbable layer of polymer, preparing a mesh and/or bundles of collagen fibers, imbuing said mesh and/or bundles with a suitable monomer compatible with the polymeric layer applied to the body, applying said fibers to form a layer on the polymeric layer, and polymerizing the monomer in situ, to anchor the collagen fibers to the polymeric layer while leaving part of the collagen fibers protruding from a surface of the implant for forming after implantation a firm bond with said surrounding tissue.

8. An implant for surgical implantation in human or veterinary medicine, adapted to form an integral structure with surrounding tissue after implantation, comprising in combination a rigid core of predetermined size and shape, at least part of the surface of which is coated with a three-layered structure, including a non-resorbable polymer layer bonded to the rigid core, a non-resorbable polymeric matrix layer wherein there are embedded and anchored collagen fibers in the form of a mesh and forming a collagen network, the interstices of the collagen network being filled with said non-resorbable polymer, and an outer surface layer formed by continuations of at least part of said embedded and anchored collagen fibers protruding from said polymeric matrix layer for forming after implantation a firm bond with said surrounding tissue.

9. An implant for surgical implantation in human or veterinary medicine, adapted to form an integral structure with surrounding tissue after implantation, comprising in combination a rigid core of predetermined size and shape, at least part of the surface of which is coated with a three-layered structure, including a non-resorbable polymer layer bonded to the rigid core, a non-resorbable polymeric matrix layer wherein there are embedded and anchored collagen fibers in the form of collagen bundles and forming a collagen network, the interstices of the collagen network being filled with said non-resorbable polymer, and an outer surface layer formed by continuations of at least part of said embedded and anchored collagen fibers protruding from said polymeric matrix layer for forming after implantation a firm bond with said surrounding tissue.

10. The implant according to claim 1, wherein said anchored collagen fibers protrude from the surface of said non-resorbable polymeric matrix a distance in a range in the order of 0.5 to 2.5 mm.

11. The implant according to claim 5, wherein the outer third layer of said anchored protruding collagen fibers has a thickness in a range on the order of 0.5 to 2.5 mm.

12. The implant according to claim 11, wherein:
the non-resorbable polymer first layer has a thickness in a range on the order of 0.5 to 5.0 mm; and
the non-resorbable polymeric matrix second layer has a thickness in a range on the order of 0.2 to 5.0 mm.

* * * * *

UNITED STATES PATENT AND TRADEMARK OFFICE
CERTIFICATE OF CORRECTION

PATENT NO. : 5,002,583
DATED : March 26, 1991
INVENTOR(S) : Pitaru, et al.

It is certified that error appears in the above-identified patent and that said Letters Patent is hereby corrected as shown below:

Column 1, in each of lines 46 and 49, "photomierograph" should read --photomicrograph--.

Figure 1:
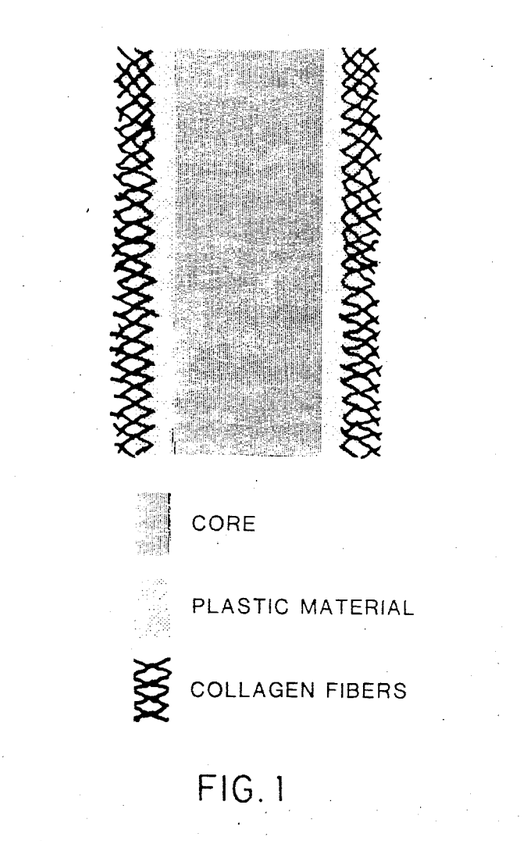
FIG. 1 is a sectional view of the implant.
Figure 2:
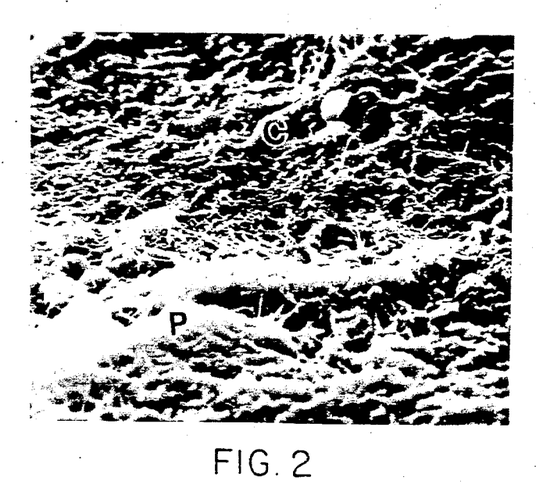
FIG. 2 is a scanning electron micrograph illustrating collagen fibers protruding from the polymer.

Column 2, line 10, after "substrate", insert --, as illustrated by the sectional view of the implant shown in Fig. 1--.

line 26, after "layers", insert --, as shown in Fig. 1--; and in line 66, after "substrate", insert --, which is further illustrated by the electron micrograph of Fig. 2, wherein the collagen fibers are shown protruding from the plastic polymer,--.

Figure 3:
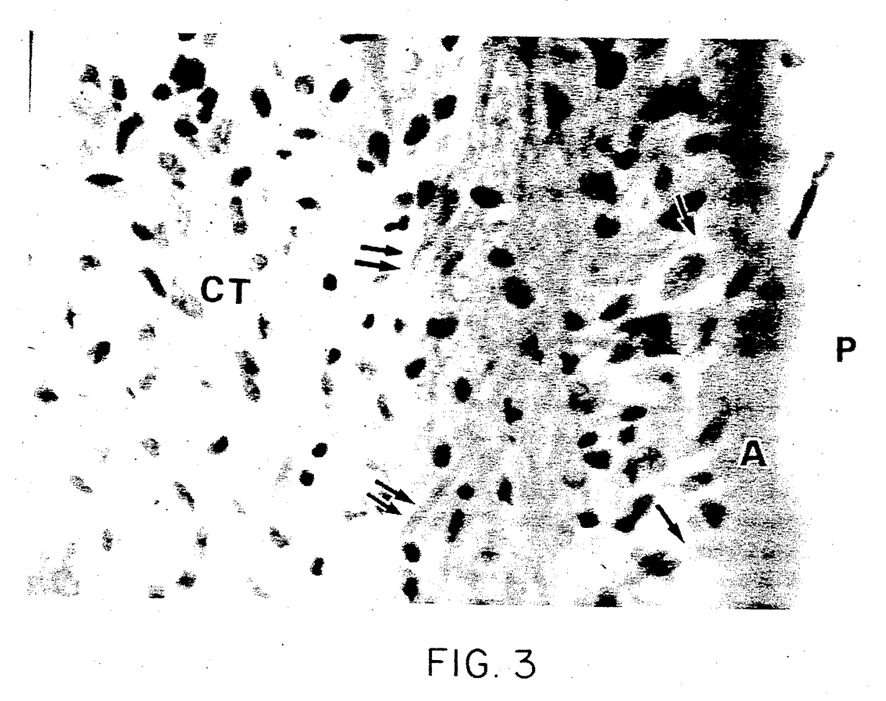
FIG. 3 is a light photomicrograph showing an histological section of the implant with new connective tissue 3 weeks after implantation.

Column 3, in line 7, at the end of the line, insert --This is illustrated by the light photomicrograph of Fig. 3, which shows a histological section of an implant with new connective tissue 3 weeks after implantation, wherein P=plastic polymer adhering to a core; A=an anchoring zone of the plastic polymer into which collagen fibers are incorporated; the single arrows indicate collagen fibers protruding from the anchoring zone A; and the double arrows indicate collagen fibers of the implant incorporated within the new connective tissue.

UNITED STATES PATENT AND TRADEMARK OFFICE
CERTIFICATE OF CORRECTION

PATENT NO. : 5,002,583

DATED : March 26, 1991

INVENTOR(S) : Sandu Pitaru, et al.

Figure 4:
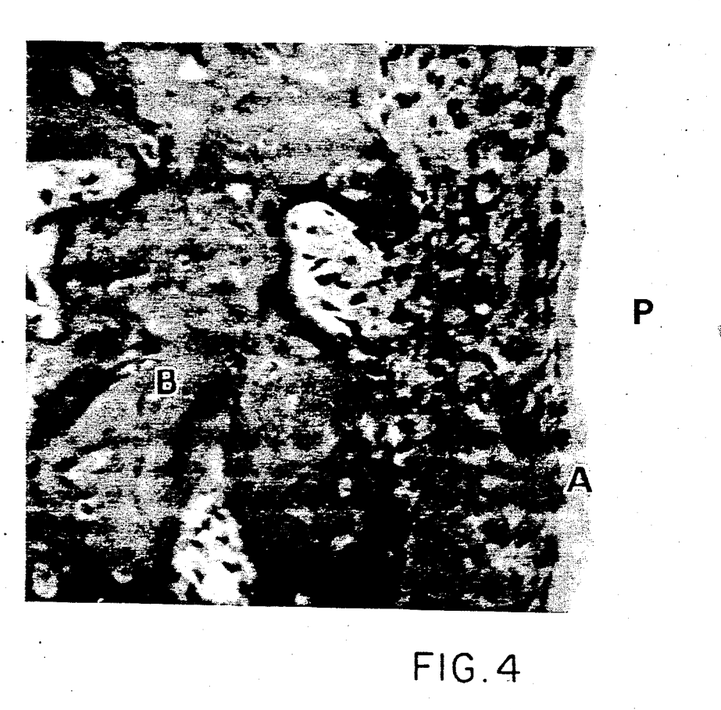
FIG. 4 is a light photomicrograph showing an histological section of the implant with fibrous connective tissue 2 months after implantation.

It is certified that error appears in the above-identified patent and that said Letters Patent is hereby corrected as shown below:

Similarly, the light photomicrograph of Fig. 4 illustrates a histological section of the implant with fibrous connective tissue 2 months after implantation, with P and A being plastic polymer and an anchoring zone, respectively, as in Fig. 3, and B being adjacent bone.--

Signed and Sealed this

Twenty-seventh Day of October, 1992

Attest:

DOUGLAS B. COMER

Attesting Officer       Acting Commissioner of Patents and Trademarks